United States Patent
Gao et al.

(10) Patent No.: US 7,358,494 B1
(45) Date of Patent: Apr. 15, 2008

(54) MATERIAL COMPOSITION ANALYSIS SYSTEM AND METHOD

(75) Inventors: Ying Gao, Santa Clara, CA (US); Moshe Sarfaty, Cupertino, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 338 days.

(21) Appl. No.: 11/153,943

(22) Filed: Jun. 15, 2005

(51) Int. Cl.
*G01N 23/00* (2006.01)
*G21K 7/77* (2006.01)

(52) U.S. Cl. ............ 250/310; 250/307; 250/311; 250/339; 250/288; 378/45; 378/46; 378/49; 378/50; 378/82; 378/83; 378/84

(58) Field of Classification Search ........ 250/307, 250/310, 311, 339.01, 288; 378/45, 46, 49, 378/50, 82, 83, 84
See application file for complete search history.

(56) References Cited

U.S. PATENT DOCUMENTS 6,787,773 B1 * 9/2004 Lee ..................... 250/311

* cited by examiner

*Primary Examiner*—Jack Berman
*Assistant Examiner*—Meenakshi S Sahu
(74) *Attorney, Agent, or Firm*—Bever, Hoffman & Harms, LLP; Jeanetter S. Harms

(57) ABSTRACT

The material composition of a thin film formed on a substrate or covered by a cap layer that shares one or more elements with the thin film can be determined by combining characteristic material data, such as characteristic x-ray data, from a material composition analysis tool, such as an electron probe-based x-ray metrology (EPMA) operation, with thickness data and (optionally) possible material phases for the thin film. The thickness data and/or the material phase options can be used to determine, for example, the penetration depth of a probe e-beam of the EPMA tool. Based on the penetration depth and the thin film thickness, the characteristic x-ray data from the EPMA operation can be analyzed to determine the composition (e.g., phase or elemental composition) of the thin film. An EPMA tool can include ellipsometry capabilities for all-in-one thickness and composition determination.

15 Claims, 4 Drawing Sheets

MATERIAL COMPOSITION ANALYSIS SYSTEM AND METHOD

BACKGROUND OF THE INVENTION

1. Field of the Invention

The invention relates to the field of semiconductor metrology, and in particular, to thin film composition determination including phase identification in multilayer structures.

2. Related Art

As modern semiconductor device geometries continue to shrink, performing metrology (i.e., determining material composition properties such as elemental distribution or molecular structure (phase)) on those devices becomes increasingly important and difficult. Currently, some of the most problematic metrology operations involve the analysis of multilayer stacks (e.g., a thin film on a substrate or multiple thin films formed on top of each other) that share one or more common elements. Conventional metrology techniques can have difficulty determining the material composition properties of such "shared element" structures since conventional techniques cannot readily distinguish between signals from the common element that originate from the different layers in the stack.

For example, to improve CMOS performance, a silicide contact layer can be created to improve electrical conductivity between transistors and metal lines (interconnects). The silicide layer is formed by depositing a metal (e.g., titanium (Ti), cobalt (Co), or nickel (Ni)) onto the polycrystalline silicon (polysilicon) gate and/or source/drain regions of a transistor, and applying an elevated temperature to form a surface layer of refractory metal silicide. The contact layer lowers the resistance of the polysilicon-interconnect interface, thereby enabling faster device performance.

Determining the phase of a silicide contact layer is of significance because phase can affect resistivity in a silicide. For example, cobalt can form at least two stable silicide phases: CoSi and $CoSi_2$. For maximum performance benefit in a silicide contact layer, it is desirable to form the $CoSi_2$ phase, which has a lower resistivity than the CoSi phase. Nickel exhibits three common phases: $Ni_2Si$, NiSi, and $NiSi_2$. Of the three, the NiSi phase has the lowest resistivity, and is therefore typically the desirable phase. Thus, the ability of metrology tools to determine the actual phase of a silicide layer is critical for the proper tuning of high performance semiconductor processes.

Traditionally, phase determinations have been made using x-ray fluorescence (XRF), x-ray diffraction (XRD), or transmission electron microscopy (TEM). XRF involves the application of a probe x-ray beam to a test sample to cause emission of characteristic x-rays from the test sample. The characteristic x-rays from the different atoms in the test sample can then be used to determine the concentrations of the different elements in the test sample. Unfortunately, XRF is a relatively slow technique (processing only a few wafers per hour at best), and is therefore not ideal for use in production line environments. Furthermore, the probe x-ray beam used in an XRF system generally produces a measurement spot size (i.e., the size of the probe beam incident upon the test sample) that is too large (>50 um) to measure high performance devices.

Finally, XRF can have problems with shared element structures. For example, a silicide contact layer over a polysilicon gate forms a multilayer structure in which both layers include silicon. Therefore, because an XRF probe x-ray beam cannot be "tuned" to only penetrate the top layer (particularly for very thin layers such as contact layers), characteristic silicon x-rays will be generated from both the silicide layer and the polysilicon layer, thereby making determination of the phase of the silicide layer impossible. Other x-ray techniques, such as x-ray diffraction (XRD), face similar problems (slow, large spot size, difficulty targeting just the layer of interest).

TEM involves sending a high-energy electron beam through a prepared test sample to determine atomic-level information about the test sample. TEM can generate accurate phase information, but is a destructive technique, due to the need to slice and thin the test sample so that sufficient electron transmission is provided. Therefore, TEM is not suitable for in-line metrology (i.e., measurements of production wafers). Other less common techniques for phase determination are generally unsuitable for in-line monitoring for similar reasons. For example, secondary ion mass spectrometry (SIMS) uses an ion beam to sputter the surface of a test sample, and then uses a mass spectrometer to analyze the sputtered particles. In this manner, an accurate determination of surface composition can be made. However, like TEM, SIMS is a destructive technique, and therefore cannot be used on production wafers.

Thus, it is desirable to provide a system and technique for performing thin film metrology on a shared element multi-layer structure in a production line environment.

SUMMARY OF THE INVENTION

Conventional systems and methods cannot effectively determine the material properties of a thin film within a multi-layer film stack. Typical nondestructive phase determination systems (e.g., XRF and XRD) are too slow, too imprecise (i.e., large spot size), and are not selective enough to provide phase detection utility in a production environment. Destructive techniques (e.g., TEM and SIMS), while able to accurately determine the phase of specific device layers, are by definition not suitable for use on in-line production monitoring. To overcome these limitations of conventional systems and techniques, an electron probe microanalysis system can be used in conjunction with layer thickness measurement data to efficiently and accurately determine material phase without any wafer-damaging effects.

In one embodiment, a method for determining an actual material phase of a thin film can involve applying an electron probe microanalysis (EPMA) operation (or any other material composition analysis operation, such as x-ray photoelectron spectroscopy (XPS), auger electron spectroscopy (AES), and XRF) to the thin film to generate a set of characteristic material data (e.g., characteristic x-ray data for EPMA or photoelectron energy spectra for XPS), and then determining model composition for the thin film based on the set of characteristic material data, the thickness of the thin film, and density values associated with trial phases for the thin film. If a model composition is substantially consistent with the trial phase used in the determination of that model composition, then that model composition can be provided as the actual material phase of the thin film. In one embodiment, this phase determination process can be performed in an iterative manner, with model composition being determined one at a time until substantial composition consistency is detected. In another embodiment, model composition can be determined for all trial phases simultaneously, and consistency checking can be performed all at once.

In another embodiment, an EPMA tool can include an e-beam generator for directing a probe e-beam at a test sample that includes a thin film formed on a substrate, an x-ray detector for measuring the set of characteristic x-rays generated by the test sample in response to the e-beam, and phase determination logic that includes modeling logic for generating a set of model composition from a set of trial phases for the thin film based on the thickness of the thin film and the set of characteristic x-rays and checking logic for determining of one of the set of model composition is substantially consistent with the one of the set of trial phases used in the generation of that model composition. In one embodiment, the checking logic can include logic for applying the modeling logic sequentially to the set of trial phases until a model composition/trial phase match is detected. In another embodiment, the checking logic can include logic for applying the modeling logic to the entire set of trial phases simultaneously to generate the set of model composition and logic for detecting a match between one of the set of model composition and the trial phase used to generate that model composition. In another embodiment, the EPMA tool can include a material phase database from which the set of trial phases can be obtained. In another embodiment, the EPMA tool can include a communications interface for receiving the thin film thickness and/or the set of trial phases. In another embodiment, the EPMA tool can include an optical metrology module (e.g., an ellipsometry module or a reflectometry module) for determining the thickness of the thin film.

The invention will be more fully understood in view of the following description and drawings.

DETAILED DESCRIPTION

Conventional systems and methods cannot effectively determine the material properties of a thin film formed on a multi-layer film stack that shares an element with top thin film. Typical nondestructive phase determination systems (e.g., XRF and XRD) are too slow, too imprecise (i.e., large spot size), and are not selective enough to provide accurate material composition determinations in a production environment. Destructive techniques (e.g., TEMS and SIMS) that can provide such material composition information are by definition not suitable for use in production line environments. To overcome these limitations of conventional systems and techniques, an electron probe microanalysis system can be used in conjunction with layer thickness data to efficiently and accurately determine material phase without any wafer-damaging effects.

Electron probe microanalysis (EPMA), which is sometimes referred to as electron microprobe analysis (EMPA), involves the measurement of characteristic x-rays emitted from a test sample in response to a probe electron beam. By analyzing the characteristic x-ray data, the thickness and/or composition of the test sample can be determined. EPMA techniques are non-destructive, relatively fast (current tools provide a throughput in the range of 15-20 wafers per hour), and can precisely target very small regions of a test sample due to the small (sub-micron) spot size of the electron beam ("e-beam") used as a probe beam, and are therefore well-suited to in-line monitoring of production wafers.

However, as a standalone system, an EPMA tool cannot address the "shared element" metrology issues described above. For example, an EPMA tool will by itself generally have difficulty in reliably detecting the material phase of a thin film formed on a substrate that shares an element with the thin film (particularly for the very thin films used in modern semiconductor devices). The e-beam will typically penetrate the thin film and interact with the underlying layer to generate a disproportionate reading for the shared element. Other compositional analysis tools (e.g., XRF) will typically be faced with similar limitations and will not be able to by themselves accurately provide material composition information in shared element film stacks. However, by applying an EPMA tool (or other compositional analysis tool) in conjunction with thickness data, accurate material composition property determinations for shared element stacks can be made.

Figure 1:
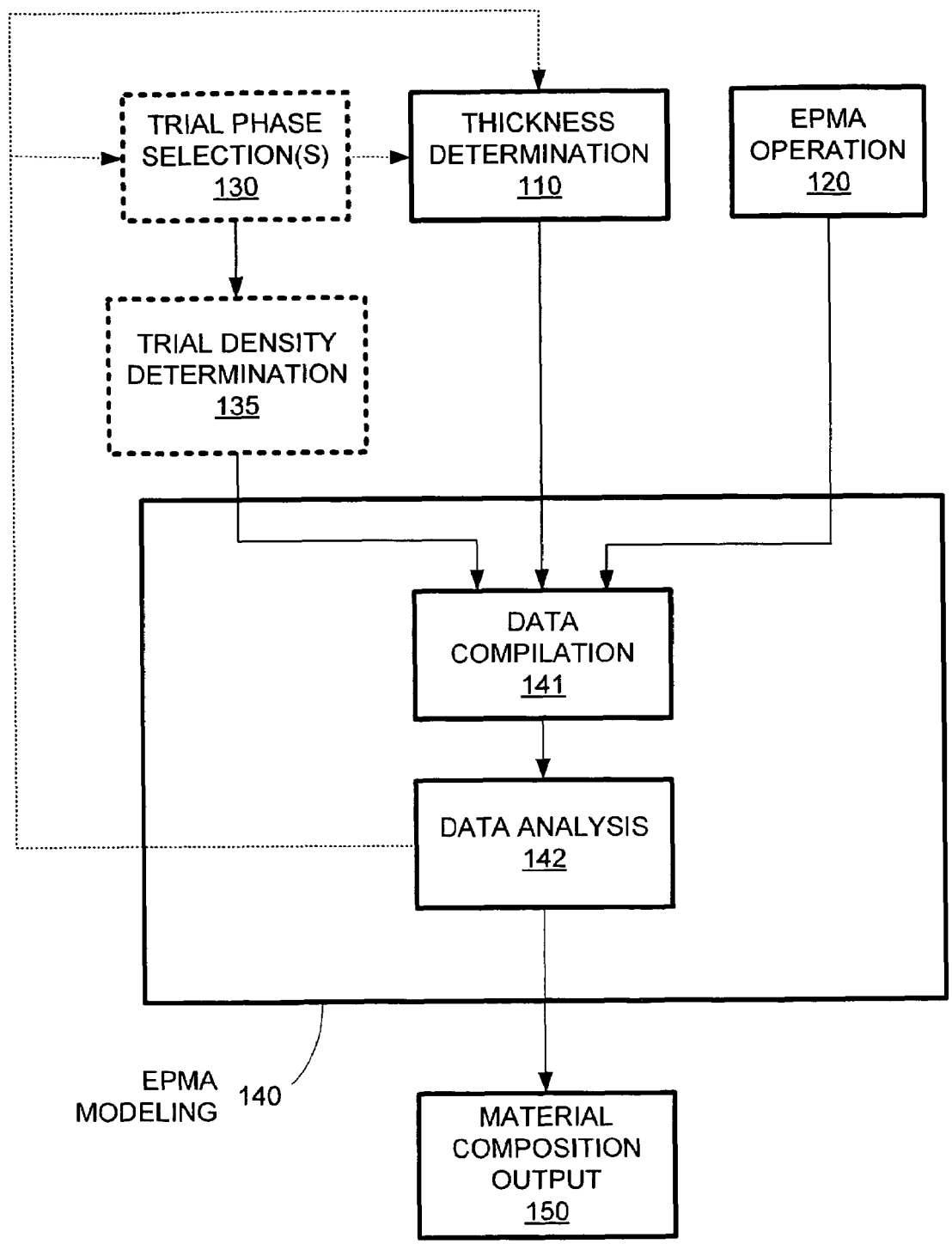
FIG. 1 is a flow diagram of an embodiment of a method for nondestructively determining material composition using an electron probe microanalysis system.

FIG. 1 shows a flow diagram of one embodiment of an EPMA-based metrology technique for determining material composition (e.g., elemental concentrations or material phase) of a thin film in a test sample. In a "THICKNESS DETERMINATION" step 110, thickness data is generated for at least one of the thin film layers on a test sample being evaluated. Note that in some embodiments, the thickness determination of step 110 can involve the thin film layer in the test sample for which the material composition is being determined. In other embodiments, the thickness determination of step 110 can involve a thin film layer in the test sample other than the thin film layer for which the material composition is being determined (as described with respect to the SiON gate example below).

In any case, the thickness data from step 110 can be obtained in any manner, such as via optical metrology (e.g., ellipsometry) or x-ray metrology (e.g., x-ray reflectometry (XRR) or grazing-incidence x-ray reflectometry (GXR)). For inline monitoring of wafers, the use of ellipsometry can be particularly beneficial, due to the relatively high throughput of ellipsometry tools (up to 50 wafers per hour).

Note that in one embodiment, the thickness data can even be obtained via the use of an expected thickness (i.e., not measured) for a well-characterized process. However, due to the sensitivity of the subsequent modeling that involves the thickness data, the use of estimated thickness data can be less than ideal.

In an "EPMA OPERATION" step 120, an EPMA operation is performed on the test sample. As noted above, the EPMA operation involves the application of an e-beam to the test sample to induce generation of characteristic x-rays from the different elements in the test sample. Note step 120 can have any temporal relationship with step 110, and can therefore, in various embodiments, be performed before, after, or during step 110.

If the material composition determination includes a material phase determination, an optional "TRIAL PHASE SELECTION(S)" step 130 can be performed, in which the various material phase possibilities and characteristics for the thin film are compiled. For example, for a nickel silicide film, the NiSi, $Ni_2Si$, and $NiSi_2$ phases could be compiled as trial phases (i.e., material phases that may represent the actual material phase of the thin film layer). Note that the trial phase selections can be entered by a user, extracted from a preexisting database of material phase data, or compiled by any other manner. Note further that step 130 can have any temporal relationship with steps 110 and 120 (e.g., before both steps 110 and 120, between steps 110 and 120, after steps 110 and 120, or during steps 110 and/or 120).

Trial densities for the trial phases compiled in step 130 can then be determined in an optional "TRIAL DENSITY DETERMINATION" step 135. Because each of the trial phases has a different molecular composition, each trial phase will be associated with a different trial density. For example, Table 1 provides a list of densities for three common nickel silicide phases.

TABLE 1

| Phase | Density (g/cm3) |
| --- | --- |
| $Ni_2Si$ | 6.71 |
| NiSi | 5.62 |
| $NiSi_2$ | 4.53 |

Using the layer thickness data from step 110, the characteristic x-ray distribution (EPMA data) from step 120, and (if applicable) the trial density data from optional step 135, the test sample is modeled in an "EPMA MODELING" step 140. Step 140 begins with a "DATA COMPILATION" step 141, in which the thickness value from step 110, the characteristic x-ray data from step 120, and the density values from step 135 (if applicable) are compiled.

Then, the characteristic material data generated in step 120 is analyzed in a "DATA ANALYSIS" step 142 to determine the desired material composition output. For example, to perform a phase determination, the trial density values gathered in step 135 (and the known density value of the substrate) are first used to determine an expected e-beam penetration depth into the test sample for each of the trial phases. The intensity (or intensities) of the characteristic x-rays from the EPMA data from step 120 can then be evaluated in light of these expected e-beam penetration depths (and the thin film thickness) to derive a calculated composition. Specifically, the trial phase that provides an expected material composition (based on expected e-beam penetration, the actual thickness, and the trial phase) that is consistent with the calculated material composition (based on expected e-beam penetration, the actual thickness, and the characteristic x-ray data) is selected as the actual phase and provided as a system output in a "MATERIAL COMPOSITION OUTPUT" step 150.

Note that while this and other embodiments of the invention are described with respect to EPMA analysis, any other composition analysis technique can be used during steps 120 and 140. For example, using an XPS-based analysis, the characteristic material data generated in step 120 would be a photoelectron energy spectrum (rather than the characteristic x-rays generated by EPMA), and the photoelectron peaks of that spectrum could be used in the modeling of step 140 (along with thickness data and the trial phase (if applicable) to determine the material composition output provided in step 150. In a similar manner, AES or XRF-based analyses could be combined with thickness and trial phase data to determine material composition.

Note further that in one embodiment, the different trial phases can be evaluated concurrently. In a concurrent process, the expected material compositions for all trial phases can be simultaneously generated and evaluated for consistency with the EPMA data. In another embodiment, the trial phases can be evaluated sequentially. In a sequential process, the expected material composition for the first trial phase is generated and compared with the calculated material composition for the first trial phase, and if a match is not detected, the expected/calculated material composition comparisons are performed for additional trial phases until a match is detected (indicated by the dotted line between steps 143 and 130). Various other comparison algorithms will be readily apparent.

Note further that certain optical thickness measurement techniques that could be used in step 110 could themselves be sensitive to material phase. Therefore, in one embodiment, the trial phase feedback path between steps 142 and 130 could also provide updated phase selection and model data to enable updating of the thickness data provided in step 110 (indicated by the dotted line between step 142 and step 110, and the dotted line between step 130 and step 110).

Note further that the particular comparison methodology used in step 142 will determine the particular matching criteria used in step 142. For example, if material phase is the basis for comparison between the expected material composition and the calculated material composition, then that model material phase will generally be required to exactly match one of the trial phases to constitute "substantial consistency". However, if the basis for comparison is an atomic percentage of a material of interest (e.g., nickel percentage for a nickel silicide layer), then that model atomic percentage may need to match an expected characteristic x-ray intensity (based on the trial phase, the thin film thickness, and the EPMA measurement parameters (e.g., e-beam power)) to within a predetermined tolerance band to indicate "substantial consistency" (e.g., atomic nickel percentage match to within +/−15%). Various other methods of performing the comparison between the model phase and the trial phase will be readily apparent.

Table 2 provides an exemplary set of phase, density, and EPMA data for two wafers that demonstrate this checking process. For example, wafer 1 in Table 2 includes a 228.74 A nickel silicide layer and wafer 2 includes a 356 A nickel silicide layer (step 110). Three trial phases $Ni_2Si$, NiSi, and $NiSi_2$ are defined for the nickel silicide layers (step 130), and those trial phases define densities 6.71 g/cm3, 5.62 g/cm3, and 4.53 g/cm3, respectively (step 135). Based on those densities and on the layer thickness (228.74 A for wafer 1 and 356 A for wafer 2), an expected characteristic x-ray intensity (specified as expected nickel percentages) can then be determined for each of the trial phases (step 141). Those expected characteristic x-ray intensity can then be compared to the actual characteristic x-ray intensity (specified as actual nickel percentages) to determine which of the trial phases provides a consistent model of the actual material phase (step 142).

For example, for wafer 1, trial phase Ni2Si dictates a trial density of 6.71 g/cm3. This trial density and the actual layer thickness of 228.74 A (along with the trial phase) define an expected nickel percentage of 66.7%. This expected nickel percentage can then be compared to the calculated nickel percentage of 31% that is determined from the trial density, the actual layer thickness, and the measured x-ray intensity for nickel taken during the EPMA process. A difference between the calculated nickel percentage and the expected nickel percentage can then be determined to evaluate the appropriateness of the initial trial phase. For example, the trial phase $Ni_2Si$ for wafer 1 results in an expected-to-actual nickel concentration difference of −36%, while trial phases NiSi and $NiSi_2$ result in differences of −10.7% and 20.9%, respectively. Based on these results, material phase NiSi, which has the smallest expected-to-actual difference, can be output as the actual material phase of the silicide layer on wafer 1. Using a similar analysis, material phase NiSi$_2$ can be output as the actual material phase of the silicide layer on wafer 2.

TABLE 2

| Wafer No. | Layer Thk. (A) | Trial Phase | Trial Density (g/cm$^3$) | Exp. Ni % | Calc. Ni % | Diff. | Match? |
|---|---|---|---|---|---|---|---|
| 1 | 228.74 | Ni$_2$Si | 6.71 | 66.7% | 31.0% | −36% | No |
|   |        | NiSi     | 5.62 | 50.0% | 39.3% | −10.7% | Yes |
|   |        | NiSi$_2$ | 4.53 | 33.3% | 54.2% | 20.9% | No |
| 2 | 356    | Ni$_2$Si | 6.71 | 66.7% | 18.8% | 47.9% | No |
|   |        | NiSi     | 5.62 | 50.0% | 23.4% | 26.6% | No |
|   |        | NiSi$_2$ | 4.53 | 33.3% | 31.0% | −2.3%$_2$ | Yes |

A similar methodology could be used for other shared-element films for which material composition is a critical parameter. For example, a phosphorous-doped polysilicon (PDP) layer can be analyzed by first determining the layer thickness (e.g., using spectroscopic ellipsometry), and then deriving the phosphorous dose in the layer by evaluating EPMA data in light of the thickness, as described above. Similarly, a silicon oxynitride (SiON) gate layer could be analyzed by determining layer thickness, performing EPMA, and evaluating the EPMA data in view of the thickness data to derive the oxygen and/or nitrogen atomic percentage in the SiON layer. Likewise, a silicon germanium boron (SiGeB) layer can be analyzed in a similar manner to determine layer thickness and germanium and/or boron concentration in the layer. Note that while the flow chart of FIG. 1 is described with respect to a phase determination for exemplary purposes, the steps in the flow chart can be applied to an EPMA-based determination of any other material composition. For example, modern CMOS devices often use a silicon oxy-nitride (SiON) gate dielectric to improve performance over conventional transistors with conventional silicon dioxide (SiO$_2$) dielectrics. To create a SiON layer with a high nitrogen concentration (resulting in a high dielectric constant), plasma-based processes are used.

However, plasma-processed films are generally not very stable when exposed to air. Therefore, a SiON film is often immediately covered with a cap layer of polysilicon to ensure dielectric integrity. Unfortunately, for the reasons described above, metrology operations on the covered SiON layer using conventional techniques are generally inadequate. However, the flow chart of FIG. 1 provides a methodology for effective determination of the composition of the covered SiON layer. In step 110, the thickness of the cap (polysilicon) layer is determined. Meanwhile, an EPMA operation is performed in step 120 to determine characteristic x-ray data for the oxygen and nitrogen in the SiON layer. The thickness data from step 110 and the x-ray data from step 120 is then compiled in step 141, and an analysis of the characteristic x-ray data in light of the thickness data is performed in step 142 to determine the oxygen and nitrogen concentrations in the SiON layer.

Specifically, the thickness data for the polysilicon cap layer can be used to determine e-beam penetration depth during the EPMA operation and an x-ray attenuation factor for the oxygen and nitrogen x-rays emitted from the SiON layer in response to the e-beam. Using these parameters, the characteristic x-ray data can then be analyzed to determine the oxygen and nitrogen concentrations in the SiON layer. In particular, the x-ray attenuation factor can be used to calculate the actual oxygen and nitrogen x-ray intensities at the surface of the SiON layer (i.e., prior to being attenuated by the cap layer of polysilicon). The actual oxygen and nitrogen x-rays intensity values are determined by the oxygen and nitrogen concentrations, respectively, in the SiON layer and the e-beam penetration depth into the SiON layer. Therefore, using the previously determined e-beam penetration depth and the calculated actual oxygen and nitrogen x-ray intensity values, the oxygen and nitrogen concentrations in the SiON layer can be determined.

Figure 2:
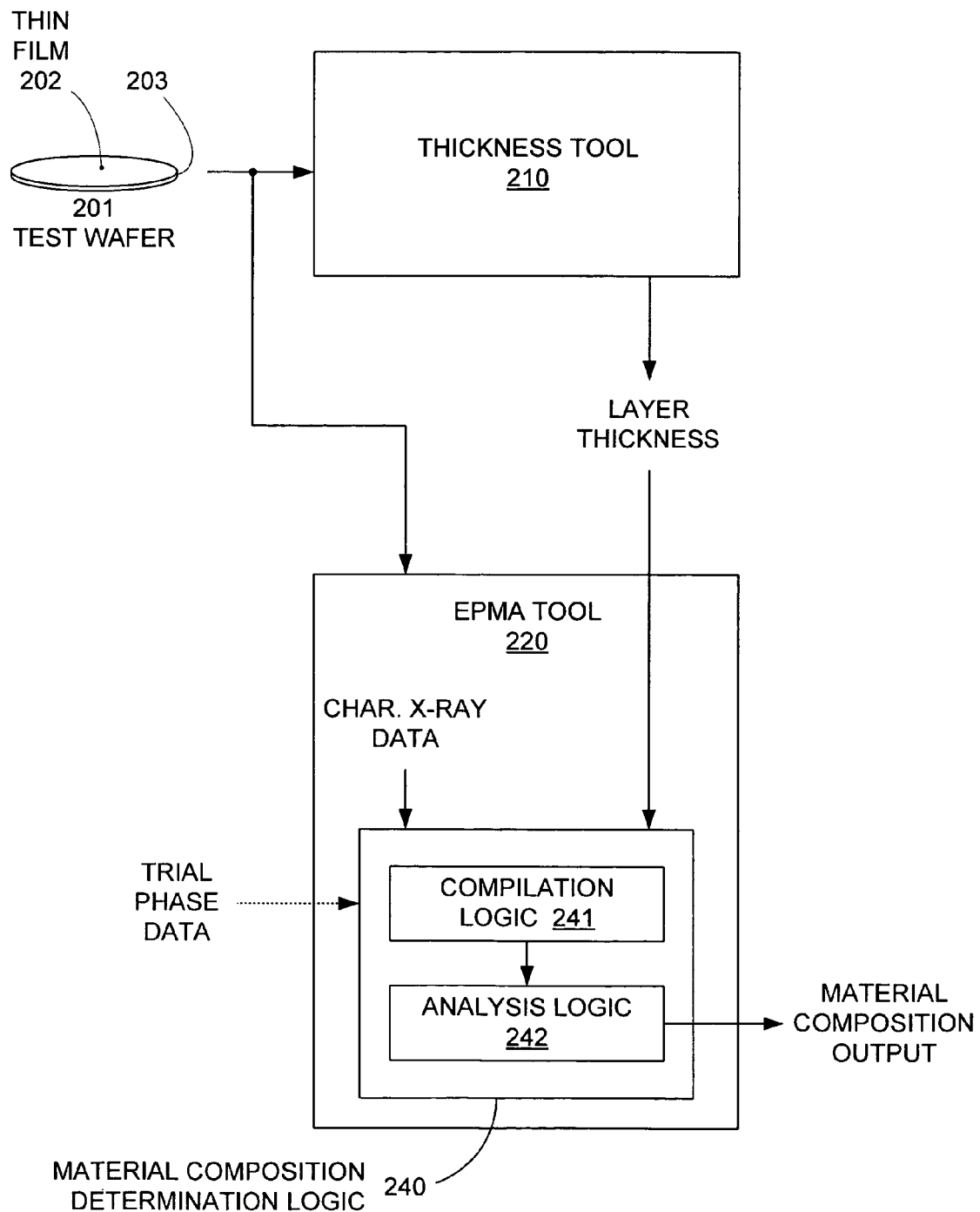
FIG. 2 is a simplified representation of one embodiment of a method for nondestructively determining material composition using an electron probe microanalysis system.

FIG. 2 shows a simplified representation of the material composition determination process described with respect to the flow chart of FIG. 1. A test wafer 201 that includes a thin film 202 (e.g. a silicide layer or a polysilicon cap layer) on a substrate 203 (e.g. a silicon wafer or a SiON layer) is processed by a thickness tool 210 (e.g., an ellipsometry tool) that determines the thickness of thin film 202 (as described above with respect to step 110 of FIG. 1). Test wafer 201 is also provided to an EPMA tool 220 for EPMA processing to generate a set of characteristic x-ray data (from either thin film 202 or from a desired portion of substrate 203 (e.g., a SiON layer under thin film 202)). Material composition determination logic 240 operating in EPMA tool 220 then processes the characteristic x-ray data in light of the layer thickness provided by thickness tool 210 and optional trial phase data (compiled as described above with respect to steps 130 and 135 of FIG. 1) to determine material composition output for thin film 202 or a desired layer in substrate 203. Note that while material composition determination logic 240 is depicted as being incorporated into EPMA tool 220 for exemplary purposes, according to various other embodiments of the invention, material composition determination logic 240 can be operated from an external location (e.g., a fab server or controller).

Material composition determination logic 240 includes compilation logic 241 and analysis logic 242. Compilation logic 241 gathers the relevant thickness data and characteristic x-ray data for the test sample (as described with respect to step 141 in FIG. 1). Analysis logic 242 can then determine the material composition for the thin film of interest in the test sample using the data collected by compilation logic 241. For example, analysis logic 242 could generate expected elemental concentrations based on input trial phase data (as described with respect to steps 130 and 135 in FIG. 1) and compare those expected results with the actual results calculated from the characteristic x-ray data (as described above with respect to Table 2) to select an actual material phase to output as the material composition output. Alternatively, analysis logic 242 could provide elemental concentrations as the material composition output by calculating those elemental concentrations in the substrate based on the thickness data and the characteristic x-ray data (as described above with respect to SiON gate dielectric example).

Note that EPMA tool 220 can have any temporal and spatial relationship with thickness tool 210. For example, in one embodiment, thickness tool 210 and EPMA tool 220 can be located in the same fab, with EPMA tool 220 measuring test wafer 201 after the thickness measurement of thickness tool 210. In another embodiment, thickness tool 210 and EPMA tool 220 could be in different fabs, with thickness tool 210 transferring layer thickness data to EPMA tool 220 via a network (e.g., a LAN or WAN). Note further that in various other embodiments, EPMA tool 220 can be replaced with any other type of composition analysis tools (e.g., XPS, AEG, or XRF), as described with respect to FIG. 1 (with appropriate adjustments to material composition determination logic 240, such as providing analysis logic for analyzing photoelectron spectra rather than characteristic x-ray data if XPS is used instead of EPMA).

Figure 3A:
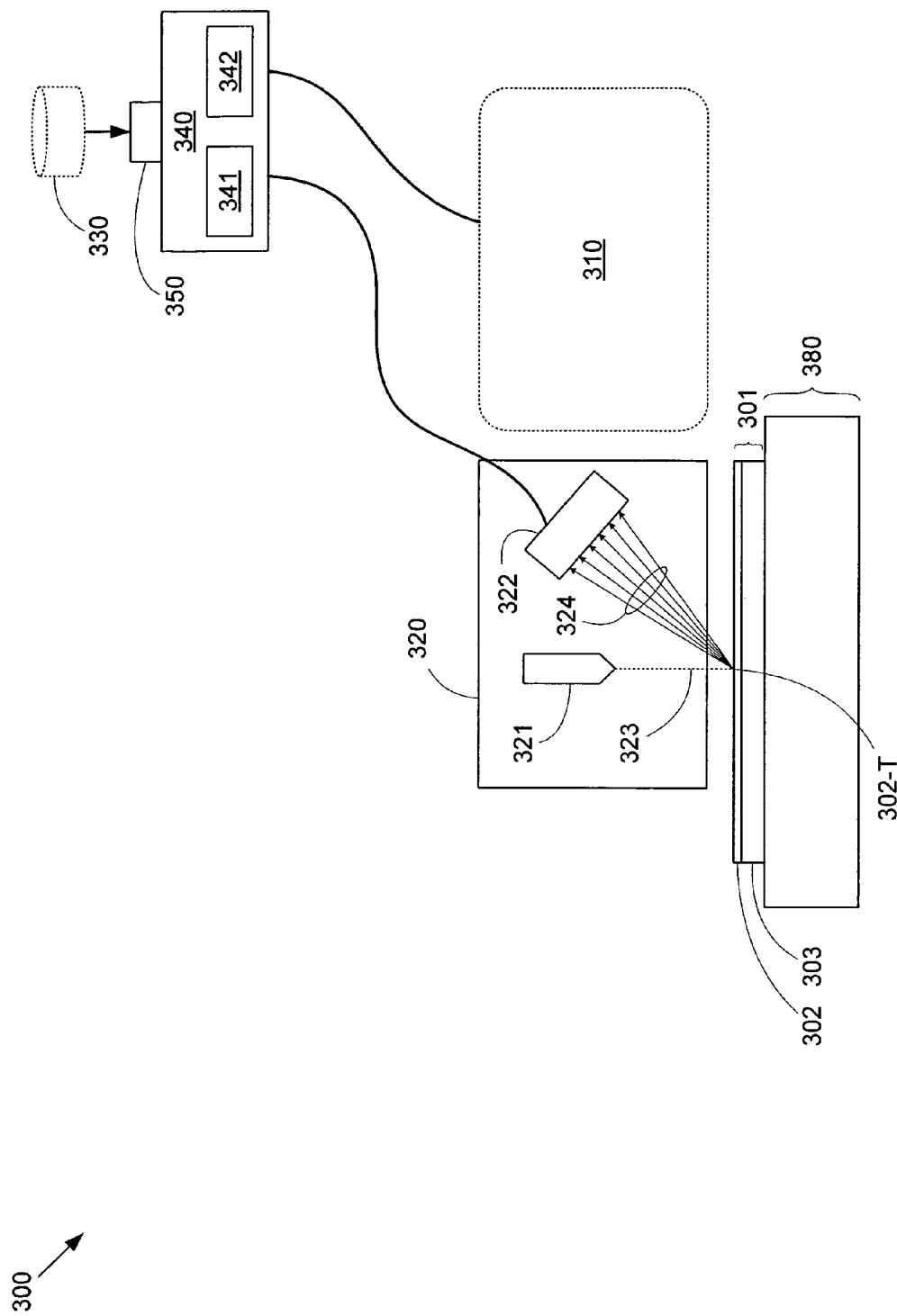
FIGS. 3A and 3B are schematic diagrams of an embodiment of a system for nondestructively determining material composition using electron probe microanalysis.

In another embodiment, thickness tool 210 and EPMA tool 220 could be combined into a single metrology tool, thereby enabling both thickness and material composition measurements to be provided by a single tool, while potentially providing even greater phase detection efficiency. For example, FIG. 3A shows a schematic diagram of a metrology tool 300 that includes an EPMA module 320, a stage 380 for supporting a test wafer 301, material composition determination logic 340, and an optional ellipsometry module 310 (indicated by the dotted line).

For exemplary purposes, EPMA module 320 includes an e-beam generator 321 and an x-ray detector 322 (such as an energy dispersive x-ray spectrometer (EDS) or a wavelength dispersive x-ray spectrometer (WDS)) for EPMA analysis. However, according to various other embodiments, EPMA module 320 can include any type of EPMA metrology equipment. Furthermore, in various other embodiments, material composition determination logic 340 can be part of ellipsometry module 310 or EPMA module 320 (e.g., incorporated into the control logic for EPMA module 320), or can be separate from measurement tools (e.g., a software program residing on a standalone computer). In addition, in various other embodiments, EPMA module 320 can be replaced with any other type of material composition analysis module (e.g., an XPS module, an AES module, or an XRF module), with appropriate adjustments made to material composition determination logic 340 (e.g., replacing logic for analyzing characteristic x-ray data with logic for analyzing photoelectron spectral data if EPMA module 320 is replaced with an XPS module).

Test wafer 301 includes a thin film 302 on a substrate 303 (e.g., a silicide layer on a single crystalline silicon substrate or a phosphorous-doped polysilicon layer over a single crystalline silicon substrate). Note that substrate 303 may itself be formed from multiple different layers. To perform a material phase determination operation on thin film 302, EPMA module 320 first performs an EPMA operation on test wafer 301. E-beam generator 321 directs an e-beam 323 at a target location 302-T on thin film 302, which results in the generation of a set of characteristic x-rays 324 that are measured by x-ray detector 322.

As described above, the characteristic x-rays 324 originates from both thin film 302 and substrate 303, thereby making direct determination of the material phase or elemental composition of thin film 302 or substrate 303 from the characteristic x-rays without known film thickness impossible. Thus, as described above with respect to FIG. 2, the characteristic x-ray data generated by EPMA module 320 is sent to material composition determination logic 340. Material composition determination logic 340 is substantially similar to material composition determination logic 240 described with respect to FIG. 2, and includes compilation logic 341 and analysis logic 342.

Compilation logic 341 behaves substantially similarly to compilation logic 241 described above with respect to FIG. 2, and gathers the relevant thickness data and characteristic x-ray data for the test sample. For example, for a phase determination of a silicide layer 302 at the surface of substrate 301, compilation logic could gather trial phase data from a trial phase source 330, thickness data from optical metrology module 310, and characteristic x-ray data from EPMA module 320. In one embodiment, metrology tool 300 can include a communications interface 350 (e.g., a network port or user interface) for receiving thickness and/or trial phase data. For example, trial phase source 330 can comprise an external database or a user that enters appropriate phase information via communications interface 350. Alternatively, trial phase source 330 could comprise a database within metrology tool 300.

In another embodiment, for an elemental composition determination of a SiON layer in substrate 301 under a polysilicon cap layer 302, compilation logic 341 could gather just the thickness data (for polysilicon cap layer 302) from optical metrology module 310 and the characteristic x-ray data (for the underlying SiON layer) from EPMA module 320. Analysis logic 342 can then either evaluate the characteristic x-ray data for consistency with the trial phases to determine material phase, or directly calculate the elemental concentration(s) from the thickness and characteristic x-ray data (as described above with respect to analysis logic 242 in FIG. 2).

Figure 3B:
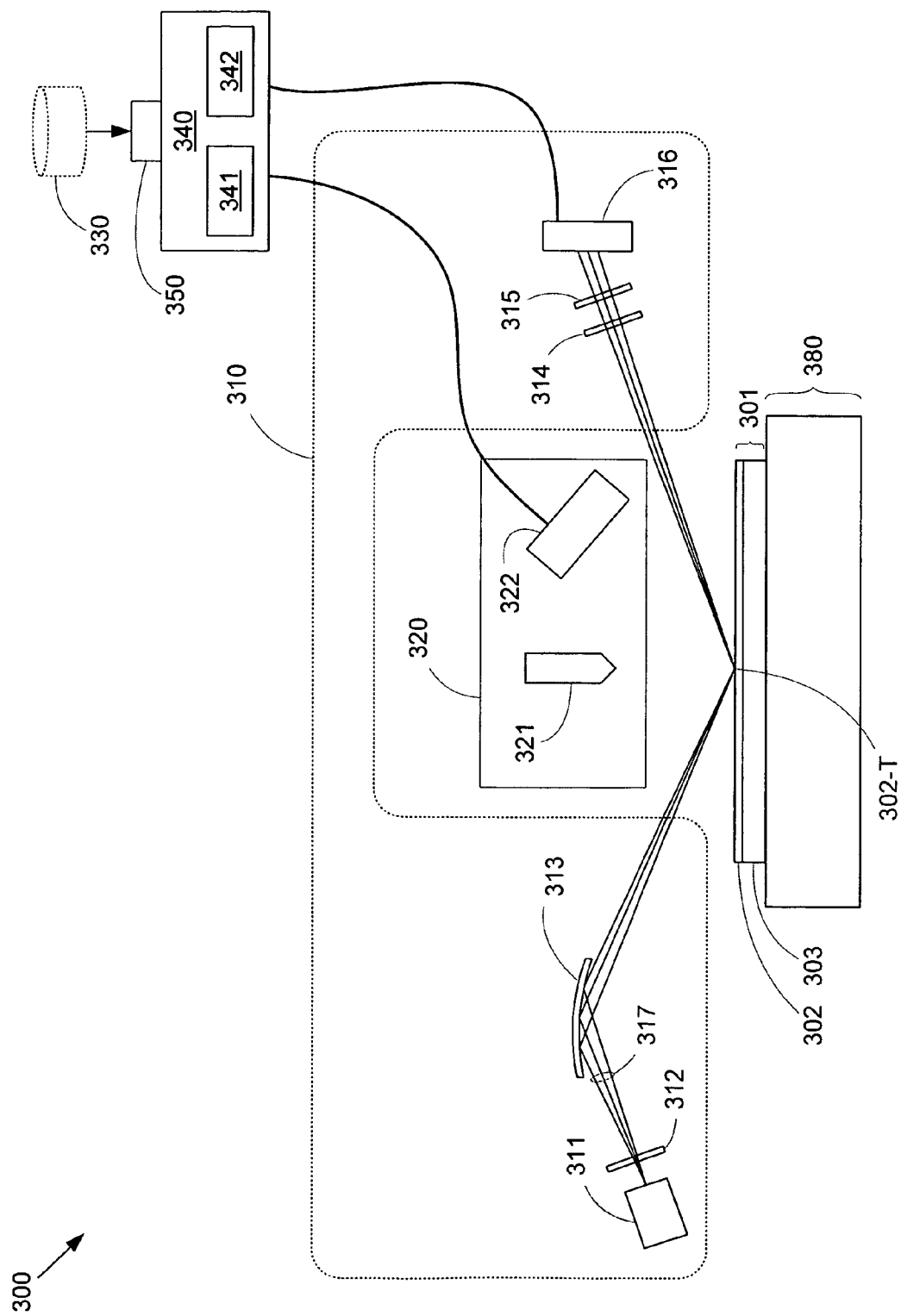

FIG. 3B shows an exemplary implementation of optical metrology module 310 that includes a xenon lamp 311, a rotating polarizer 312, focusing optics 313, a fixed polarizer 314, a spectrometer 315, and a CCD detector 316 for performing a spectroscopic ellipsometry analysis. To perform a thickness measurement, xenon lamp 311 directs a diverging light beam 317 through rotating polarizer 312 at focusing optics 313, which reflect and focus beam 247 onto target location 302-T on thin film 302. Light beam 247 is reflected by thin film layer 302 as a diverging beam, which passes through fixed polarizer 314 and spectrometer 315 before being measured by CCD detector 316 to allow the thickness of thin film 302 to be determined. This thickness data can then be provided to phase selection logic 340 for use in the determination of the phase of thin film 302, as described with respect to FIG. 3A. Note that while optical metrology module 310 is depicted as providing spectroscopic ellipsometry capabilities for exemplary purposes, according to various other embodiments of the invention, optical metrology module 310 can provide any type of optical metrology capability (e.g., reflectometry).

Although the invention has been described in connection with several embodiments, it is understood that the invention is not limited to the embodiments disclosed, but is capable of various modifications that would be apparent to one of ordinary skill in the art. Thus, the invention is limited only by the following claims and their equivalents.

The invention claimed is:

1. A method for determining a material composition for a thin film layer in a test sample, the method comprising:
    applying an electron probe microanalysis (EPMA) operation to the thin film layer to generate a set of characteristic x-rays; and
    generating an output value for the material composition based on the set of characteristic x-rays and a measured thickness value for a test layer in the test sample,
    wherein the test layer is the thin film layer, wherein the material composition is material phase, and wherein generating the output value comprises:
        identifying a first one of a plurality of trial phases for the thin film layer defining an expected composition that is substantially consistent with a calculated composition, the expected composition being based on the first one of the plurality of trial phases, a density for the test layer defined by the first one of the plurality of trial phases, and the measured thickness value for the test layer, and the calculated composition being based on the set of characteristic x-rays, the measured thickness value for the thin film layer, and the density for the test layer; and providing the first one of the plurality of trial phases as the output value.

2. The method of claim 1, wherein identifying the first one of the plurality of trial phases comprises:
selecting a test one of the plurality of trial phases;
determining a density for the test one of the plurality of trial phases;
deriving an expected composition for the test one of the plurality of trial phases based on the density and the measured thickness value, and the test one of the plurality of trial phases;
comparing the expected composition of the test one of the plurality of trial phases to a calculated composition of the test one of the plurality of trial phases, the calculated composition of the test one of the plurality of trial phases being derived from the set of characteristic x-rays, the measured thickness value, and the density;
repeating the steps of selecting, determining, deriving, and comparing until the expected composition for the test one of the plurality of trial phases is consistent with the calculated composition of the test one of the plurality trial phases; and
assigning the test one of the plurality of trial phases as the first one of the plurality of trial phases.

3. The method of claim 2, wherein identifying the first one of the plurality of trial phases further comprises updating the measured thickness value according to the test one of the plurality of trial phases.

4. The method of claim 1, wherein identifying the first one of the plurality of trial phases comprises:
generating a set of expected compositions for the plurality of trial phases, each of the set of expected compositions being determined by one of the plurality trial phases, a density defined by the one of the plurality of trial phases and the measured thickness value;
generating a set of calculated compositions for the plurality of trial phases, each of the set of calculated compositions being determined by the set of characteristic x-rays, the measured thickness value, and the density defined by the one of the plurality of trial phases;
comparing each of the set of expected compositions for the plurality of trial phases to an associated one of the set of expected compositions for the plurality of trial phases to determine the first one of the plurality of trial phases.

5. The method of claim 4, wherein generating a set of expected compositions for the plurality of trial phases comprises adjusting the measured thickness value based on the one of the plurality of trial phases, and
wherein generating a set of calculated compositions for the plurality of trial phases comprises adjusting the measured thickness value based on the one of the plurality of trial phases.

6. The method of claim 1, wherein the thin film layer comprises one of a silicide layer formed over a single crystalline silicon substrate, a phosphorous-doped polysilicon layer formed over the single crystalline silicon substrate, a silicon germanium boron layer formed over the single crystalline silicon substrate, and a silicon oxy-nitride layer formed over the single crystalline silicon substrate.

7. An electron probe microanalysis (EPMA) tool comprising:
an e-beam generator for directing an e-beam at a test sample, the test sample comprising a thin film formed on a substrate;
an x-ray detector for measuring a set of characteristic x-rays generated by the test sample in response to the e-beam; and
material composition determination logic for determining a material composition of the thin film, the material composition determination logic comprising:
compilation logic for compiling measured thickness data for a test layer in the test sample and the set of characteristic x-rays; and
analysis logic for determining a material composition for the thin film based on the measured thickness data for the test layer and the set of characteristic x-rays,
wherein the test layer is the thin film, and wherein the analysis logic comprises:
logic for identifying a first one of a plurality of trial phases for the thin film, the first one of the plurality of trial phases defining an expected composition that is substantially consistent with a calculated composition for the first one of the plurality of trial phases; and
logic for providing the first one of the set of trial phases as the material phase of the thin film,
wherein the expected composition is based on the first one of the plurality of trial phases, a density for the test layer defined by the first one of the plurality of trial phases, and the measured thickness data for the test layer, and
wherein the calculated composition for the first one of the plurality of trial phases is based on the set of characteristic x-rays, the density, and the measured thickness data for the test layer.

8. The EPMA tool of claim 7, wherein the logic for identifying the first one of the plurality of trial phases comprises:
logic for selecting a test one of the plurality of trial phases;
logic determining a density for the test one of the plurality of trial phases;
logic for generating an expected composition for the test one of the plurality of trial phases based on the density, the measured thickness data for the test layer, and the test one of the plurality of trial phases;
logic for comparing the expected composition of the test one of the plurality of trial phases with a calculated composition of the test one of the plurality of trial phases, the calculated composition of the test one of the plurality of trial phases being derived from the set of characteristic x-rays, the measured thickness data for the test layer, and the density;
logic for repeatedly applying the logic for selecting, the logic for determining, the logic for generating, and the logic for comparing until the expected composition of the test one of the plurality of trial phases is consistent with the calculated composition of the test one of the plurality of trial phases; and
logic for assigning the test one of the plurality of trial phases as the first one of the plurality of trial phases.

9. The EPMA tool of claim 7, further comprising a material phase database for providing the set of trial phases.

10. The EPMA tool of claim 7, further comprising a communications interface for receiving at least one of the set of trial phases and the thickness of the thin film.

11. The EPMA tool of claim 7, wherein the thin film comprises one of a silicide layer formed over a single crystalline silicon substrate and a phosphorous-doped polysilicon layer formed over the single crystalline silicon substrate.

12. A system for determining a material composition of a thin film in a test sample, the system comprising:
　　means for compiling a set of characteristic material data generated by directing a probe beam at the thin film, the means for compiling the set of characteristic material data comprising an electron probe microanalysis module;
　　means for compiling measured thickness data for a test layer in the test sample; and
　　means for determining the material composition using the set of characteristic material data and the measured thickness data,
　　wherein the test layer comprises the thin film, and
　　wherein the means for determining the material composition comprises:
　　　　means for identifying a first one of a plurality of trial phases for the thin film layer, the first one of the plurality of trial phases defining an expected composition that is substantially consistent with a calculated composition for the first one of the plurality of trial phases; and
　　　　providing the first one of the plurality of phases as the material composition,
　　wherein the expected composition is based on the first one of the plurality of trial phases, a density for the test layer defined by the first one of the plurality of trial phases, and the measured thickness data for the test layer, and
　　wherein the calculated composition for the first one of the plurality of trial phases is based on the set of characteristic material data, the density, and the measured thickness data for the test layer.

13. The system of claim 12, further comprising means for accessing a material phase database to compile the set of trial phases.

14. The system of claim 12,
　　wherein the probe beam comprises an e-beam, and
　　wherein the set of characteristic material data comprises a set of characteristic x-rays.

15. The system of claim 12, further comprising means for performing optical metrology on the test sample to generate the measured thickness data for the test layer.

* * * * *